United States Patent [19]

Mewshaw et al.

[11] Patent Number: 5,750,556

[45] Date of Patent: May 12, 1998

[54] 2-(AMINOMETHYL)-3,4,7,9-TETRAHYDRO-2H-PYRANO-[2,3-E]INDOL-8-ONES AND DERIVATIVES

[75] Inventors: Richard E. Mewshaw, Princeton, N.J.; Gary P. Stack, Ambler, Pa.

[73] Assignee: American Home Products Corporation, Madison, N.J.

[21] Appl. No.: 739,917

[22] Filed: Oct. 30, 1996

[51] Int. Cl.⁶ .................. A61K 31/40; A61K 31/44; C07D 491/052; C07D 491/00
[52] U.S. Cl. .................. 514/411; 514/291; 514/215; 548/432; 546/89; 540/521
[58] Field of Search .................. 548/429, 432; 546/89; 540/521; 514/215, 291, 411

[56] References Cited

U.S. PATENT DOCUMENTS

| | | |
|---|---|---|
| 4,314,944 | 2/1982 | Huffman et al. |
| 5,318,988 | 6/1994 | Schole-Loop et al. |
| 5,371,094 | 12/1994 | Heine et al. |

OTHER PUBLICATIONS

Tamminga et al., "Dopamine Agonist Treatment of Schizophrenia With N-Propylnorapomorphine", Psychiatry, 398–402, 1986.

Tamminga et al., "Schizophrenic Symptoms Improve with Apomorphine", Science, 200, 567–568, 1978.

Lahti et al., "Intrinsic Activity Determinations at the Dopamine D2 Guanine Nucleotide–Binding Protein–Coupled Receptor: Utilization of Receptor State Binding Affinities", Mol. Pharm., 42, 432–438, 1993.

Corsini et al., "Sedative, Hypnotic, and Antipsychotic Effects of Low Doses of Apomorphine in Man", Adv. Biochem. Psychopharmacology, 16, 645–648, 1997.

*Primary Examiner*—Deborah Lambkin
*Attorney, Agent, or Firm*—Rebecca R. Barrett

[57] ABSTRACT

Compounds of Formula I are selective autoreceptor agonists useful in treating disease states involving hyperactivity of dopamine systems:

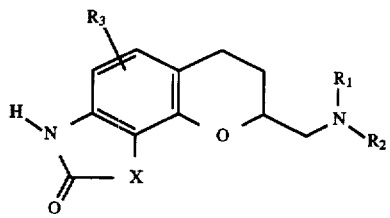

in which X is $-(CH_2)_n-$; n is 1–3; $R_1$ is hydrogen, alkyl, hydroxyalkyl, cycloalkyl-methyl, bicyclo-alkylmethyl or $-(CH_2)_m YAr$; where m is 0–4, Y is $-CH_2-$, and Ar is phenyl, halophenyl, alkylphenyl, dialkylphenyl or alkoxyphenyl; $R_2$ is hydrogen or alkyl; $R_3$ is hydrogen, halogen, alkyl, alkoxy or hydroxy; or a pharmaceutically acceptable salt thereof.

13 Claims, No Drawings

2-(AMINOMETHYL)-3,4,7,9-TETRAHYDRO-2H-PYRANO-[2,3-E]INDOL-8-ONES AND DERIVATIVES

This application claims the benefit of U.S. application Ser. No. 60/007,307, filed Nov. 6, 1995.

BACKGROUND OF INVENTION

Efforts to induce antipsychotic activity with dopamine autoreceptor agonists have been successful (Corsini et al. Adv. Biochem. Psychopharmacol 16, 645–648, 1977; Tammitinga et al. Science 200, 567–568, 1978; and Tamminga et al. Psychiatry 398–402, 1986). A method for determining intrinsic activity at the dopamine $D_2$ receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compound's ability to elicit an antipsychotic effect.

U.S. Pat. No. 4,314,944 to Huffman and Wilson describes a series of indolones which are useful for cardiovascular abnormalities. U.S. Pat. No. 5,318,988 and No. 5,371,094 to Bayer claims a series of fused ring-benzopyrans which are potentially useful for the treatment of central nervous system diseases.

DESCRIPTION OF INVENTION

In accordance with this invention, there is provided a group of compounds which are useful antipsychotic agents. The compounds of this invention are essentially free from extrapyramidal side effects (EPS). The compounds of this invention are selective autoreceptor agonists, functioning primarily to activate only autoreceptors versus postsynaptic $D_2$ dopamine receptors). As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing a well as inhibition of dopamine synthesis and release and therefore provide a means of controlling hyperactivity of the dopaminergic systems.

More specifically, the compounds of this invention are depicted by the following Formula I:

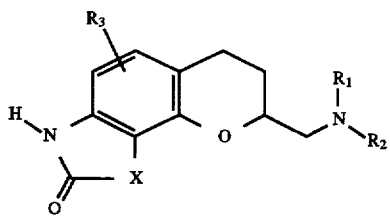

I in which:

X is —$(CH_2)_n$—;

n is 1–3;

$R_1$ is hydrogen, alkyl of 1 to 6 carbon atoms, hydroxyalkyl of 1 to 6 carbon atoms, cycloalkylmethyl of 4 to 9 carbon atoms, bicyclo-alkylmethyl of 7 to 9 carbon atoms or —$(CH_2)_m YAr$; where m is 0–4, Y is —$CH_2$—, and Ar is phenyl, halophenyl, alkylphenyl where the alkyl substituent has 1 to 6 carbon atoms, dialkylphenyl where each alkyl substituent, independently, has 1 to 6 carbon atoms or alkoxyphenyl where the alkoxy substituent has 1 to 6 carbon atoms;

$R_2$ is hydrogen or alkyl of 1 to 6 carbon atoms;

$R_3$ is hydrogen, halogen, alkyl of 1 to 6 carbon atoms, alkoxy of 1 to 6 carbon atoms or hydroxy;

or a pharmaceutically acceptable salt thereof.

Preferred compounds of Formula I are those in which $R_1$ is benzyl, halobenzyl, alkylbenzyl, in which one or two alkyl groups are present, each alkyl substituent having, independently, 1 to 6 carbon atoms, alkoxybenzyl having from 1 to 6 carbon atoms in the alkoxy substituent or cyclohexylmethyl. The most preferred values of the alkyl and alkoxy substituents are those having 1 to 3 carbon atoms. The most preferred halogens are chlorine, bromine and fluorine.

The pharmaceutically acceptable acid addition salts are prepared by methods well known to the art from either inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric, hydrobromic, sulfuric, cyclohexylsulfamic, phosphoric, nitric acids, and similar acids.

Some of the compounds of this invention are racemates which may be resolved into d and l enantiomers by standard methods.

The compounds of Formula I are generally prepared by the overall sequence indicated in Scheme I as follows:

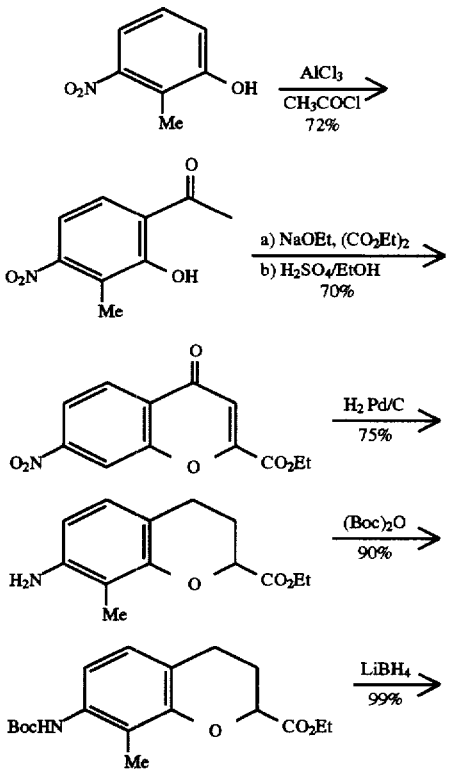

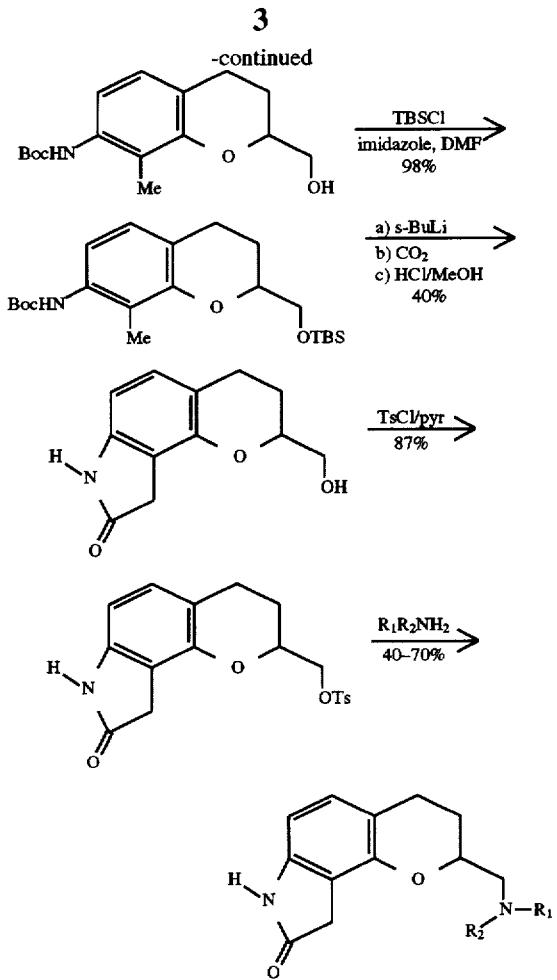

The following examples showing the preparation of representative compounds of this invention are presented by way of illustration rather than limitation.

EXAMPLE 1

2-(Benzylamino-methyl)-3,4,7,9-tetrahydro-2H-pyrano-[2,3-e]indol-8-one

To a 5L round-bottom flask equipped with a mechanical stirrer, nitrogen inlet and temperature controlled heating mantle was added 2-methyl -3-nitrophenol (210 g, 1.37 mol), nitrobenzene (1680 mL), and acetyl chloride (127 mL, 1.79 mol). The reaction mixture was warmed up to 45° C. and a small amount of aluminum chloride was added and the reaction was stirred at 45° C. for 1 hour. After another portion of aluminum chloride (183 g, 1.37 mol) was added, the temperature rose to 60° C. and the reaction mixture was slowly heated to 120° C. and stirred for 16 hours. The reaction mixture was cooled in an ice bath to 15° C. and a saturated aqueous solution of sodium chloride (2 L) was added slowly, keeping the temperature below 25° C. The organic layer separated and was diluted with toluene, filtered over Solka Floc® to remove tar impurities, and washed with water. More tar impurties precipitated and the mixture was again filtered over Solka Floc®. The organic layer was separated and washed with 0.5 N sodium hydroxide (4×1L). The combined aqueous layers were filtered over Solka Floc®, and acidified by slow addition of concentrated hydrochloric acid (240 ml). The product was extracted in methylene chloride, dried with $MgSO_4$, charcoalized, and the solvent was removed to afford 193 g of 2-hydroxy-3-methyl-4-nitro-acetophenone as a thick oil which solidified upon standing: mp 40°–41° C.

Elemental Analysis for $C_9H_9NO_4$

Calculated: C, 55.39; H, 4.65; N, 7.18

Found: C, 55.30; H, 4.53; N, 7.06

To a 5L 3-neck round-bottom flask, equipped with a mechanical stirrer and nitrogen inlet was added diethyl oxalate (167 mL, 1.23 mol) and 21% sodium ethoxide in ethanol (840 mL, 2.25 mol). After cooling the mixture in an ice water bath for 10 minutes, a solution of 2-hydroxy-3-methyl-4-nitro-acetophenone (192.8 g, 0.99 mol) in ethanol (775 mL) was added under vigorous stirring. The solution became thick, solidified, and the temperature was increased to 50° C. for 3 hours while the mixture was stirred. A solution of concentrated sulfuric acid (80 mL) in ethanol (280 mL) was added slowly, and the reaction mixture was allowed to reflux for 1.5 hours, then stirred overnight at room temperature. Sodium acetate (77 g) was added and the mixture was stirred for 20 minutes, followed by the dropwise addition of water (280 mL). After stirring for 20 minutes, the solids were filtered and washed with ethanol/water (60/40). The solid was triturated in water for 1 hour, collected by filtration, washed with water and dried in a vacuum oven to afford 193 g (0.696 mol, 70%) of 8-methyl-7-nitro-4-oxo-4H-chromene-2-carboxylic acid ethyl ester. This product was taken on to the next step without further purification: mp 119.5°–120° C.

Elemental Analysis for $C_{13}H_{11}NO_6$

Calculated: C, 56.32; H, 4.00; N, 5.05

Found: C, 56.36; H, 3.86; N, 4.88

A mixture of 8-methyl-7-nitro-4-oxo-4H-chromene-2-carboxylic acid ethyl ester (42.2 g, 0.152 mol) and palladium on carbon (4.7 g) in glacial acetic acid was hydrogenated at 50 psi for 48 hours. The catalyst was filtered through Celite® and the solvent removed under high vacuum. The crude product was chromatographed (25% ethyl acetate in hexanes) to afford 24.5 g (0.104 mol, 68.4%) of 7-amino-8-methyl-chroman-2-carboxylic acid ethyl ester as an orange oil which solidified upon standing: mp 82°–85°C.

Elemental Analysis for $C_{13}H_{17}NO_3$

Calculated: C, 66.36;H, 7.28; N, 5.95

Found: C, 66.28; H, 7.33; N, 5.86

To a solution of 7-amino-8-methyl-chroman-2-carboxylic acid ethyl ester (7.4 g, 31.5 mmol) in anhydrous tetrahydrofuran (40 mL) at 0° C. was added a solution of di-t-butyl-dicarbonate (7.21g, 33.0 mmol) in anhydrous tetrahydrofuran (30 mL). The reaction was allowed to warm to ambient temperature and stirred for an additonal 24 hours. The reaction mixture was diluted with diethyl ether (150 mL) and washed with water (80mL), brine (50 mL), dried over anhydrous magnesium sulfate, filtered, and the solvent removed. Purification by chromatography (15% ethyl acetate-hexane) afforded 9.48 g (28.3 mmol, 89.9%) of 7-tert-butyloxycarbonylamino-8-methyl-chroman-2-carboxylic acid ethyl ester as a white solid: mp 123°–124° C.

Elemental analysis for $C_{18}H_{25}NO_5$

Calculated: C, 64.46; H, 7.51; N, 4.18

Found: C, 64.52; H, 7.61; N, 4.15

To a solution of 7-tert-butyloxycarbonylamino-8-methyl-chroman-2-carboxylic acid ethyl ester (9.4 g, 28.0 mmol) in anhydrous tetrahydrofuran (70 mL) was slowly added a 2.0M solution of lithium borohydride (33.6 mL, 67.3 mmol). The reaction was allowed to stir for 24 h then quenched by the cautious addition of methanol (15 mL). The reaction mixture was allowed to stir another 1 h, upon which time water (250 mL) was added and the mixture extracted with ether (2×400 mL). The organic layer was separated, dried over anhydrous magnesium sulfate, filtered, and the solvent removed. Purification by flash chromatography (50% ethyl-acetate-hexanes) afforded 7-(tert-butyloxycarbonylamino-8-methyl-chroman-2-yl)-methanol (12.3 g ;99%) as a thick oil.

A mixture of 7-(tert-butyoxycarbonylamino-8-methyl-chroman-2-yl)-methanol (7.2 g, 24.5 mmol), t-butyldimethylsilyl chloride (4.07, 27.0 mmol), and imidazole (5.06 g, 73.6 mmol) in anhydrous dimethylformamide (50 mL) was stirred for 15 hours, then poured into water (200 mL) and extracted with diethyl ether (2×150 mL). The organic layers were combined and washed again with water (80 mL), brine (80 mL), dried over anhydrous magnesium sulfate, filtered, and the solvent evaporated. Purification by flash chromatography afforded [2-(tert-butyl-dimethyl-silanyloxymethyl)-8-methyl-chroman-7-yl]-carbamic acid tert-butyl ester as a clear oil which solidifies upon standing: mp 61.5°–62° C.

Elemental analysis for $C_{22}H_{37}NO_4Si$

Calculated: C, 64.83; H, 9.15; N, 3.44

Found: C, 64.78; H, 9.20; N, 3.32

To a solution of [2-(tert-butyl-dimethyl-silanyloxymethyl)-8-methyl-chroman-7yl]-carbamic acid tert-butyl ester (10.0 g, 24.6 mmol) in anhydrous tetrahydrofuran (120 mL) containing 10 mg of 1,10-phenanthroline at −40° C. was slowly added 49.3 mL of 1.3M s-butyl lithium (after 24 mL of s-butyl lithium was added the deep red color of the indicator became apparent). The reaction was allowed to stand for 1.5 hours after which carbon dioxide was bubbled into the solution for 30 minutes. The reaction was quenched with 1 N HCl (4 mL) and the solvent was removed. The dark oil was dissolved in methanol (80 mL) containing water (8 ml), followed by the addition of 1 mL of concentrated hydrochloric acid. The reaction mixture was allowed to reflux for 24 hours whereupon the methanol was evaporated and the reaction mixture was diluted with water (80 mL). The mixture was extracted with methylene chloride (3×200 mL) and the combined organic layers were dried over anhydrous magnesium sulfate, filtered, and the solvent removed under vacuum to afford an orange-tan solid. Trituration with diethyl ether afforded 2.13 g of 2-(3,4,7,9-tetrahydro-2H-pyrano[2,3e]indol-8-one)-methanol: mp 214°–215° C.

To a solution of 2-(3,4,7,9-tetrahydro-2H-pyrano[2,3-e]indol-8-one)-methanol (1.97 g, 9.0 mmol) in anhydrous pyridine (20 mL) was added p-tolylsulfonyl chloride (3.43 g, 18.0 mmol). The reaction was allowed to stir for 2 hours at room temperature then quenched with water (10 mL). After stirring for 30 minutes the reaction mixture was diluted with methylene chloride (300 mL) and washed with 1 N hydrochloric acid (2×150 mL). The organic layer was washed with water (80 mL) followed by saturated aqueous sodium bicarbonate (50 mL). The organic layer dried over anhydrous magnesium sulfate, filtered, and the solvent evaporated to afford a tan solid. Trituration with methylene chloride-diethyl ether (1:1, 50 mL) afforded 2-(p-tolylsulfonylmethyl)-3,4,7,9-tetrahydro-2H-pyrano[2,3e]indol-8-one as a light tan solid (1.84 g). Concentration of the mother liquor and trituration afforded another crop of product (490 mg). The mother liquor was again concentrated, followed by column chromatography (3% methanol-methylene chloride) to afford another 331 mg of product as an orange solid. Total yield: 87%; mp 209.5°–210.5° C.

A mixture of 2-(p-tolylsulfonylmethyl)-3,4,7,9-tetrahydro-2H-pyrano[2,3e]indol-8-one (1.1 g, 2.95 mmol) and benzylamine (631 mg, 5.89 mmol) in anhydrous dimethyl sulfoxide (15 mL) containing triethylamine (2.95 mmol) was heated at 78° C. for 12 hours. The reaction mixture was then poured into methylene chloride (150 mL) and extracted with water (2×80 mL). The aqueous layer was basified with 50% aqueous potassium carbonate and the aqueous layer washed with methylene choride (100 mL). The combined organic layers were dried over anhydrous magnesium sulfate, filtered, and the solvent concentrated. Purification by chromatography (5% methanol-methylene chloride) afforded 567 mg (62%) of the title compound as a red-orange oil which solidified upon standing: mp 128°–129°0 C. The oxalate salt was prepared in tetrahydrofuran: mp 254°–255° C.

Elemental analysis for $C_{19}H_{20}N_2O_2 \cdot C_2H_2O_4 \cdot 0.5\ H_2O$

Calculated: C, 61.91; H, 5.69; N, 6.88

Found: C, 62.14; H, 5.49; N, 6.75

The following compounds were prepared in a similar fashion using 4-fluorobenzyl-amine, 4-methoxybenzylamine, 4-methylbenzylamine, 4-chlorobenzylamine and 2,4-dimethylbenzylamine:

(1b) 2-(4-Fluoro-benzylamino-methyl)-3,4,7,9-tetrahydro-2H-pyrano[2,3-e]indol-8-one The oxalate salt was prepared for analysis (58% yield): mp 256°–259° C.

Elemental Analysis for $C_{19}H_{19}N_2O_2F \cdot C_2H_2O_4$

Calculated: C, 60.57; H, 5.08; N, 6.73

Found: C, 60.18; H, 4.97; N, 6.55

(1c) 2-(4-Methoxy-benzylamino-methyl)-3,4,7,9-tetrahydro-2H-pyrano[2,3e]indol-8-one The oxalate, hemihydrate was prepared and analyzed: mp 247°–248° C.

Elemental Analysis for $C_{20}H_{22}N_2O_3 \cdot C_2H_2O_4 \cdot 0.5\ H_2O$

Calculated: C, 60.41; H, 5.76; N, 6.40

Found: C, 60.57; H, 5.66; N, 6.21

(1d) 2-(4-Methyl-benzylamino-methyl)-3,4,7,9-tetrahydro-2H-pyrano[2,3-e]indol8-one The oxalate salt was prepared for analysis, mp 249°–250° C.

Elemental Analysis for $C_{20}H_{22}N_2O_2 \cdot C_2H_2O_4$

Calculated: C, 64.07; H, 5.87; N, 6.79

Found: C, 64.22; H, 5.98; N, 6.89

(1e) 2-(4-Chloro-benzylamino-methyl)-3,4,7,9-tetrahydro-2H-pyrano[2,3-e]indol-8-one The oxalate salt was prepared for analysis, mp 250°–250.5° C.

Anal for $C_{19}H_{19}N_2O_2Cl \cdot C_2H_2O_4$

Calculated: C, 58.27; H, 4.89; N, 6.47

Found: C, 58.66; H, 5.06; N, 6.15

(1f) 2-(2,4-Dimethyl-benzylamino-methyl)-3,4,7,9-tetrahydo-2H-pyrano[2,3-e]indol-8-one The oxalate salt was prepared for analysis, mp 245°–246° C.

Elemental Analysis for $C_{21}H_{24}N_2O_2 \cdot C_2H_2O_4$

Calculated: C, 64.78; H, 6.15; N, 6.57.

Found: C, 64.53; H, 6.12; N, 6.59.

EXAMPLE 2

Resolution of (+)-2-(Benzylamino-methyl)-3,4,7,9-tetrahydro-2H pyrano[2,3-e]indol-8-one (+)-2-(Benzylamino-methyl)-3,4,7,9-tetrahydro-2H-pyrano[2,3-e]indol-8-one (440 mg), prepared according to Example 1, was submitted to semipreparative HPLC containing a Chiralcel AS® column by using eighteen injections over a two day period and eluting (0.5 mL/min, pressure 50 bar, detection at 280 nm) with ethanol. The first peak at 17.4 minutes was collected to afford (2a) (+)-2-(benzylaminomethyl)-3,4,9-tetrhydro-2H-pyrano[2,3-e]indol-8-one (188 mg) as a clear thick oil (99.7% optical purity): $[\alpha]^{25}$+66.2°(c 1.0, CHCl$_3$). The (+)-free base (165 mg) was treated with fumaric acid in isopropanol to afford 176 mg of the hemifumarate, quarter hydrate, mp 203°–204° C., $[\alpha]^{25}$+54.3°(c 1.04, DMSO).

Elemental Analysis for $C_{19}H_{20}N_2O_2 \cdot 0.5C_4H_4O_4 \cdot 0.25 H_2O$

Calculated: C, 68.00; H, 6.11; N, 7.55
Found: C, 68.25; H, 5.98; N, 7.51

The second peak isolated with a retention time of 27.3 minutes was collected to afford (2b) (–)-2-(benzylaminomethyl)-3,4,7,9-tetrhydro-2H-pyrano[2,3-e]indol-8-one (198 mg) as a clear thick oil (99.8% optical purity): $[\alpha]^{25}$ –69.2° (c, 1.0, CHCl$_3$). The (–)-free base (153 mg) was treated with fumaric acid in isopropanol to afford 165 mg of hemifumarate, quarter hydrate, mp 201°–202° C., $[\alpha]^{25}$–57.6° (c 1.03, DMSO).

Elemental Analysis for $C_{19}H_{20}N_2O_2 \cdot 0.5C_4H_4O_4 \cdot 0.25 H_2O$

Calculated: C, 68.00; H, 6.11; N, 7.55
Found: C, 68.08; H, 5.94; N, 7.45

The compounds of this invention are dopamine autoreceptor agonists, that is, they serve to modulate the synthesis and release of the neurotransmitter dopamine. They are useful for the treatment of disorders of the dopaminergic system, such as schizophrenia, Parkinson's disease, hyperprolactinemia, depression, and Tourette's syndrome. As partial agonists at the postsynaptic dopamine D$_2$ receptor, these compounds are also useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with [$^3$H]-quinpirole (Quin.) at various concentrations of test compound, filtered, washed and counted in a Betaplate scintillation counter.

High affinity for the dopamine D$_2$ receptor was established by the standard experimental test procedure of Fields, et al., Brain Res., 136, 5789 (1977) and Yamamura et al., ed., Neurotransmitter Receptor Binding, Raven Press, N.Y. (1978) wherein homogenized limbic brain tissue is incubated with [$^3$H]-spiperidone at various concentrations of test compound, filtered washed, and shaken with Hydrofluor scintillation cocktail (National Diagnostics) and counted in a Packard 460 CD scintillation counter.

The results of the tests with compounds representative of this invention are given below.

| Example No. | IC$_{50}$ (nM) D$_2$ Qmin. | IC$_{50}$ (nM) D$_2$ Spiper | IC$_{50}$ (nM) 5-HT$_{1a}$. | IC$_{50}$ (nM) $\alpha_1$ | Ratio antagonist |
|---|---|---|---|---|---|
| 1a | 0.73 | 142 | 34 | 244 | 194 |
| 1b | 0.83 | 310 | 16 | 352 | 375 |
| 1c | 0.96 | 295 | 38 | 258 | 307 |
| 1d | 0.45 | 103 | 10 | 194 | 229 |
| 1e | 0.65 | 148 | 7.53 | 184 | 233 |
| 1f | 2.62 | 392 | 15 | 81 | 150 |
| 2a | 16.4 | 734 | 329.5 | 519 | 45 |
| 2b | 0.27 | 71.5 | 17.07 | 330 | 265 |

Hence, the compounds of this invention effect the synthesis of the neurotransmitter dopamine and thus are useful in the treatment of dopaminergic disorders such as schizophrenia, Parkinson's Disease, hyperprolactinemia, depression, Tourette's Syndrome, alcohol addiction, cocaine addiction, and addiction to analogous drugs.

The compounds of this invention may be administered orally or parenterally, neat or in combination with conventional pharmaceutical carriers. Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient. The treatment of substance abuse follows the same method of subjective drug administration under the guidance of the attending physician. Based upon the potency of the compounds of this invention as reported above, the human dose lies between about 5 to about 100 mg/day. As is

What is claimed is:

1. A compound of formula I

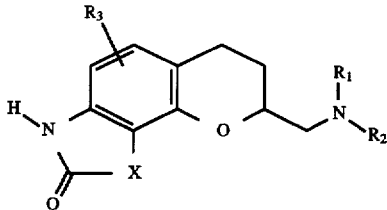

in which:

X is —(CH$_2$)$_n$—;

n is 1–3;

R$_1$ is hydrogen, alkyl of 1 to 6 carbon atoms, hydroxyalkyl of 1 to 6 carbon atoms, cycloalkylmethyl of 4 to 9 carbon atoms, bicyclo-alkylmethyl of 7 to 9 carbon atoms or —(CH$_2$)$_m$YAr; where m is 0–4, Y is —CH$_2$—, and Ar is phenyl, halophenyl, alkylphenyl where the alkyl substituent has 1 to 6 carbon atoms, dialkylphenyl where each alkyl substituent, independently, has 1 to 6 carbon atoms or alkoxyphenyl where the alkoxy substituent has 1 to 6 carbon atoms;

R$_2$ is hydrogen or alkyl of 1 to 6 carbon atoms;

R$_3$ is hydrogen, halogen, alkyl of 1 to 6 carbon atoms, alkoxy of 1 to 6 carbon atoms or hydroxy;

or a pharmaceutically acceptable salt thereof.

2. A compound of claim 1 in which n is 1; R$_1$ is benzyl, halobenzyl, alkylbenzyl, in which one or two alkyl groups are present, each alkyl substituent having, independently, 1 to 3 carbon atoms, alkoxybenzyl having from 1 to 3 carbon atoms in the alkoxy substituent or cyclohexylmethyl; or a pharmaceutically acceptable salt thereof.

3. The compound of claim 1 which is 2-(benzylaminomethyl)-3,4,7,9-tetrahydro-2H-pyrano[2,3-e]indol-8-one or a pharmaceutically acceptable salt thereof.

4. The compound of claim 1 which is (+)-2-(benzylaminomethyl)-3,4,7,9-tetrhydro-2H-pyrano[2,3-e]indol-8-one or a pharmaceutically acceptable salt thereof.

5. The compound of claim 1 which is (−)-2-(benzylaminomethyl)-3,4,7,9-tetrhydro-2H-pyrano[2,3-e]indol-8-one or a pharmaceutically acceptable salt thereof.

6. The compound of claim 1 which is 2-(4-fluorobenzylamino-methyl)-3,4,7,9-tetrahydro-2H-pyrano[2,3-e]indol-8-one or a pharmaceutically acceptable salt thereof.

7. The compound of claim 1 which is 2-(4-methoxybenzylamino-methyl)-3,4,7,9-tetrahydro-2H-pyrano[2,3-e]indol-8-one or a pharmaceutically acceptable salt thereof.

8. The compound of claim 1 which is 2-(4-methylbenzylamino-methyl)-3,4,7,9-tetrahydro-2H-pyrano[2,3-e]indol-8-one or a pharmaceutically acceptable salt thereof.

9. The compound of claim 1 which is 2-(4-chlorobenzylamino-methyl)-3,4,7,9-tetrahydro-2H-pyrano[2,3-e]indol-8-one or a pharmaceutically acceptable salt thereof.

10. The compound of claim 1 which is 2-(2,4-dimethylbenzylamino-methyl)-3,4,7,9-tetrahydo-2H-pyrano[2,3-e]indol-8-one or a pharmaceutically acceptable salt thereof.

11. A pharmaceutical composition of matter comprising a compound of the formula:

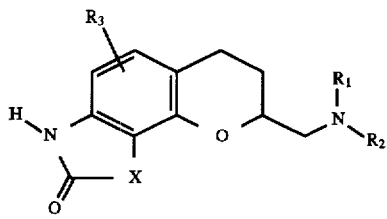

in winch:

X is —(CH$_2$)$_n$—;

n is 1–3;

R$_1$ is hydrogen, alkyl of 1 to 6 carbon atoms, hydroxyalkyl of 1 to 6 carbon atoms, cycloalkylmethyl of 4 to 9 carbon atoms, bicyclo-alkylmethyl of 7 to 9 carbon atoms or —(CH$_2$)$_m$YAr; where m is 0–4, Y is —CH$_2$—, and Ar is phenyl, halophenyl, alkylphenyl where the alkyl substituent has 1 to 6 carbon atoms, dialkylphenyl where each alkyl substituent, independently, has 1 to 6 carbon atoms or alkoxyphenyl where the alkoxy substituent has 1 to 6 carbon atoms;

R$_2$ is hydrogen or alkyl of 1 to 6 carbon atoms;

R$_3$ is hydrogen, halogen, alkyl of 1 to 6 carbon atoms, alkoxy of 1 to 6 carbon atoms or hydroxy;

or a pharmaceutically acceptable salt thereof and a pharmaceutically acceptable carrier therefor.

12. A method for reducing dopamine synthesis and release in a patient suffering from hyperactivity of the dopaminergic systems, which comprises administering to said patient a compound of the formula:

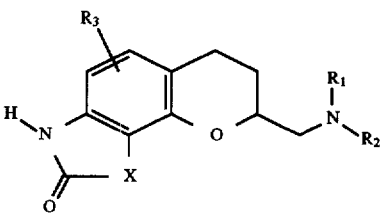

in which:

X is —(CH$_2$)$_n$—;

n is 1–3;

R$_1$ is hydrogen, alkyl of 1 to 6 carbon atoms, hydroxyalkyl of 1 to 6 carbon atoms, cycloalkylmethyl of 4 to 9 carbon atoms, bicyclo-alkylmethyl of 7 to 9 carbon atoms or —(CH$_2$)$_m$YAr; where m is 0–4, Y is —CH$_2$—, and Ar is phenyl, halophenyl, alkylphenyl where the alkyl substituent has 1 to 6 carbon atoms, dialkylphenyl where each alkyl substituent, independently, has 1 to 6 carbon atoms or alkoxyphenyl where the alkoxy substituent has 1 to 6 carbon atoms;

R$_2$ is hydrogen or alkyl of 1 to 6 carbon atoms;

R$_3$ is hydrogen, halogen, alkyl of 1 to 6 carbon atoms, alkoxy of 1 to 6 carbon atoms or hydroxy;

or a pharmaceutically acceptable salt thereof, in an amount sufficient to modulate the dopamine systems of the brain.

13. A method for treating schizophrenia which comprises administering to a patient suffering from schizophrenia, orally or parenterally, a compound of the formula:

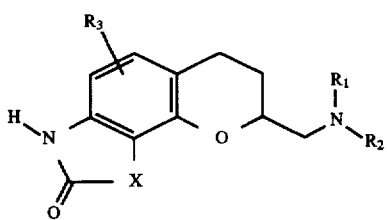

in which:

X is —(CH$_2$)$_n$—;

n is 1–3;

R$_1$ is hydrogen, alkyl of 1 to 6 carbon atoms, hydroxyalkyl of 1 to 6 carbon atoms, cycloalkylmethyl of 4 to 9 carbon atoms, bicyclo-alkylmethyl of 7 to 9 carbon atoms or —(CH$_2$)$_m$YAr; where m is 0–4, Y is —CH$_2$—, and Ar is phenyl, halophenyl, alkylphenyl where the alkyl substituent has 1 to 6 carbon atoms, dialkylphenyl where each alkyl substituent, independently, has 1 to 6 carbon atoms or alkoxyphenyl where the alkoxy substituent has 1 to 6 carbon atoms;

R$_2$ is hydrogen or alkyl of 1 to 6 carbon atoms;

R$_3$ is hydrogen, halogen, alkyl of 1 to 6 carbon atoms, alkoxy of 1 to 6 carbon atoms or hydroxy;

or a pharmaceutically acceptable salt thereof, in an amount sufficient to alleviate the symptoms of schizophrenia.

* * * * *